Figure 1:
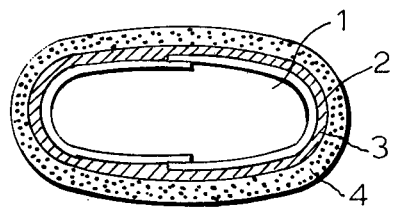

United States Patent
Watanabe et al.

[11] 3,976,764
[45] Aug. 24, 1976

[54] SOLID THERAPEUTIC PREPARATION REMAINING IN STOMACH

[75] Inventors: Sumio Watanabe; Masanori Kayano, both of Honjo; Yoshio Ishino, Kumagaya; Kohei Miyao, Tokyo, all of Japan

[73] Assignee: Eisai Co., Ltd., Tokyo, Japan

[22] Filed: Mar. 11, 1975

[21] Appl. No.: 557,408

[30] Foreign Application Priority Data
Mar. 12, 1974 Japan .............................. 49-27673

[52] U.S. Cl. .................................. 424/19; 424/32; 424/35
[51] Int. Cl.² .......................................... A61K 9/22
[58] Field of Search ....................... 424/19, 32, 35

[56] References Cited
UNITED STATES PATENTS 3,418,999  12/1968  Davis .................................. 424/14
3,870,790  3/1975  Lowey et al. .......................... 424/19

FOREIGN PATENTS OR APPLICATIONS 142,638  3/1948  Australia .............................. 424/37
1,454,013  9/1966  France ................................ 424/19

Primary Examiner—Frederick E. Waddell
Attorney, Agent, or Firm—Wenderoth, Lind & Ponack

[57] ABSTRACT

A solid therapeutic preparation for gastric diseases, remaining in stomach for a long period of time and gradually releasing pharmacologically active ingredient contained therein into gastric juice while remaining in stomach, is provided which has been prepared by impregnation of the active ingredient together with other suitable additives into a body of empty globular shell or a granular lump in small size of the material having high buoyancy. The persisting effect of the active ingredient in stomach is thus attained.

9 Claims, 6 Drawing Figures

SOLID THERAPEUTIC PREPARATION REMAINING IN STOMACH

This invention relates to a solid therapeutic preparation for internal use remaining in stomach for a long period of time and gradually releasing an active ingredient contained therein into gastric juice while remaining, said preparation having been prepared by impregnation of the active ingredient into a body of empty globular shell or a granular lump in small size of a material having high buoyancy.

It is known that essential part of a therapeutic preparation when administered per os, although there is a certain difference depending upon an individual difference and/or physiological condition of the patient to be treated, usually passes away from the stomach to large intestine through duodenum and small intestine after 1 to 2 hours from the time the said preparation was administered.

Under the conditions as abovementioned, a therapeutic preparation, the pharmacological activity of which should be exhibited in stomach for a long time, such as a gastric acid-secretion inhibitor, a gastric acid neutralizer and an anti-pepsin inhibitor as well as other medical preparations to be absorbed through wall of the stomach, would not be satisfactorily displayed, when they are administered per os in a form of customary therapeutic preparation. The fact is inexpedient because the preparations must be administered several times in an interval of 1–2 hours. In addition, there is a drawback that the residual portion of the active ingredient that did not release into gastric juice from the administered preparation while staying in the stomach only for a relatively short time may subsequently dissolve out in the intestines and behave an injurious by-effect.

At present, there is unavailable in the market a therapeutic preparation which would overcome the abovementioned drawbacks.

There is an unusual case that is known, where a certain elongation of such a retention time in stomach of an administered therapeutic preparation is attained when a therapeutic preparation of a relatively large size having a diameter larger than that of pylorus is employed. However, because the diameter of pylorus differs with one another of the individual patients, and because the retention time in the stomach of the administered preparation is largely affected by the physiological condition of the stomach under treatment, on the one hand, and by the characteristics of the active ingredient contained in the preparation, on the other hand, such an administration method of the preparation is less reliability. In addition, there is a difficulty in administration per os of a tablet or capsule in large sizes. The method is thus not adapted for the purpose of practical utility.

As the result of broad investigations effected by the present inventors for the establishment of a solid therapeutic preparation which is capable of releasing of an active ingredient contained therein for a long period of time when the same is brought into contact with gastric juice in stomach, it has been found that the purposed therapeutic preparation can be obtained by impregnating the active ingredient into a body of empty globular shell or a granular lump in small size of a material having high buoyancy.

Accordingly, the object of the present invention is to provide a solid therapeutic preparation for internal use, which is remaining in a form of a suspension in gastric juice of stomach for an elongated period of time and is capable of a gradual release of said active ingredient into the gastric juice throughout the remaining time.

As is understood from the above explanation, it is essential that the solid preparation for internal use of the present invention should have an ability of suspension for a long period of time in gastric juice of stomach as aforementioned. The contemplated preparation may thus be produced either by suitably adhering as a crust of coating containing a desired pharmacological compound on external and/or internal surfaces of an empty shell such as conventional soft or hard capsule having an apparent density less than that of gastric juice in the stomach or by impregnating the active ingredient into a granular lump in small size of a material having a high buoyancy floatable in gastric juice.

In case where an empty globular shell such as soft and hard capsules made of gelatin is employed as the carrying base or supporting substratum, said capsule may be covered with a crust by immediately applying thereon a coating material which contains an active ingredient, or more usually by first covering said capsule with a under coating of a high molecular polymer such as a cellulose acetate phthalate and an acrylic and methacrylic acids copolymer and then crusting it with a layer of coating by applying thereon with a coating material which contains an active ingredient.

In another embodiment of the invention, the opening of a deep concave shell such as a half of two pieces for forming a compositive capsule is plugged with a flat, tablet containing an active ingredient and sealed with a binding agent such as ethyl cellulose dissolved in 1,1,1-trichloroethane.

In one practice of the invention, wherein a material having buoyancy sufficient to float in gastric juice is employed, a porous granular lump in relatively small size made of foamed polystyrol or an expanded grain such as pop-rice and pop-corn is crusted with a thin layer containing an active ingredient to form a composite solid mass which is floatable in gastric juice in stomach.

In further embodiments of the invention, an empty solid mass may be prepared with a material containing an active ingredient, or a foam of a material containing active ingredient may be prepared which is floatable in gastric juice.

One of the characteristics worth criticism of the pharmaceutical preparation of the invention relies upon its enhanced durability in stomach as it floats in gastric juice when administered, independent of the individual difference between the patients under treatment, the physiological condition of stomaches, the natures of the contents in the stomach to which the preparation encounters, and the like, and the other of the characteristics relies upon the fact that the releasing rate of the active ingredient from said preparation while floating in gastric juice can be controlled at one's discretion by suitably altering the formulation of the preparation and/or the method for application of the coating material.

An additional beneficial effect achievable by the pharmaceutical preparation of the invention is the fact that the intended floating and the gradual releasing of the active ingredient contained in the preparation in gastric juice can be attained even if the solid preparation is provided in a form of relatively small sizes, and accordingly, the preparation in such a form can be easily administered per os.

The abovementioned beneficial effects achievable in the pharmaceutical preparation of the invention is proved by the following referential experiment which has been carried out by using barium sulfate provided for X-ray inspection.

Three small lumps of about 50 mg of barium sulfate respectively are placed in the hard capsules of Nos. 1, 2 and 3 prescribed in Japanese Pharmacopoeia, the 8th edition. The external surfaces of the resulting capsules were then coated with a liquid coating material consisting of 5 parts of cellulose acetate phthalate, 2 parts of barium sulfate, 20 parts of ethyl alcohol and 75 parts of acetone by spray-pan method to obtain the crusts of solid coating on the surfaces, the crust on the No. 1 capsule weighing about 203 mg, the crust on the No. 2 capsule weighing about 164 mg, and the crust on the No. 3 capsule weighing about 98 mg.

The coated capsules had the characteristics shown in the following Table:

Table 1

| Capsules | Total weights (mg) | Volumes (ml) | Apparent specific gravities |
| --- | --- | --- | --- |
| No. 3 | 200 | 0.403 | 0.496 |
| No. 2 | 280 | 0.568 | 0.493 |
| No. 1 | 330 | 0.711 | 0.464 |

Method for the administration:

Three coated capsules were respectively and orderly administered per os together with 100 ml of water to the normal adult male persons A, B and C of the following physical characteristics, the persons, before 30 minutes the administrations, having taken a conventional meal arranged with 100 g of bean paste soup, 100 g of hard boiled meat, a bit of pickle, and 200 g of boiled rice.

Table 2

| Male persons | Weights of bodies (kg) | Height (cm) | Ages | Types of Appearance |
| --- | --- | --- | --- | --- |
| A | 58 | 160 | 36 | slightly corpulent |
| B | 65 | 175 | 27 | standard |
| C | 65 | 178 | 33 | slender |

Results of the photographical observations through X-ray:

The X-ray photographs were taken just after the administrations and then successively after 15 minutes, 30 minutes, 1 hour and 3 hours from the time of the administrations and found thereby that the three capsules even though the 3 hours lapse stayed in the upper positions of the respective stomachs. No appreciable diminutions in the sizes of the capsules were found.

Following Examples together with the accompanying drawings will serve to illustrate the invention, but should be construed that the invention is not restricted by these Examples.

The accompanying drawings involving FIGS. 1 to 6 show the respective sectional views of the typical embodiments of the finished preparations of the invention.

EXAMPLE 1

External surfaces of No. 1 hard capsules prescribed in Japanese Pharmacopoeia, the 8th edition, are sprayed by spray gun with a liquid coating material consisting of 5 parts of a copolymer of cellulose acetate-phthalate, 20 parts of ethyl alcohol and 75 parts of acetone to produce 15 mg per capsule of an under coating.

The coated capsules are then further coated with a liquid mixture of 0.5 parts of propantheline bromide, 3 parts of ethylcellulose, 1.5 parts of hydroxypropyl cellulose, 70 parts of 1,1,1-trichloroethane and 25 parts of ethyl alcohol by using a spray gun and on a usual coating pan to produce a coating layer containing 5 mg of the propantheline bromide per capsule.

The resulting coated capsules are floatable in gastric juice, and from the floating capsule the propantheline bromide dissolves out gradually in the gastric juice for a long period of time.

FIG. 1 in the accompanying drawings shows a sectional view of said coated capsule wherein 1 is the hollow, 2 is the body of capsule, 3 is the under coating consisting of cellulose acetate-phthalate copolymer, and 4 is the final coating of the propantheline bromide-containing ethyl cellulose-hydroxypropyl cellulose.

EXAMPLE 2

Small lumps in oval shape of polystyrol foam each having an approximate dimension of 6 mm × 9 mm diameters are coated with about 5 mg per lump of under coating of sugar by treating with a 67% syrup. The resulting sugar-crusted lumps are then coated by using a spray gun and a fluidized-bed with a liquid mixture consisting of 0.5 parts of benactyzine hydrochloride, 2.5 parts of hydroxypropyl methyl cellulose phthalate, 2 parts of corn-starch and 95 parts of a mixture of acetone and ethyl alcohol in equi-volumetric proportions to produce the final coating on the lumps, each of which carries about 2 mg of benactyzine hydrochloride.

The products thus obtained are floatable in gastric juice for a long period of time while gradually releasing in the gastric juice the benactyzine hydrochloride by dissolving out from said finished coating.

Figure 2:
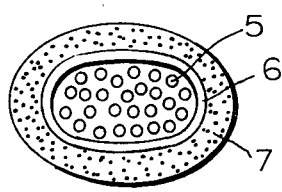

Accompanying FIG. 2 shows a sectional view of the coated product of this Example wherein 5 is the allipsoid of polystyrol foam, 6 is the under coating of sugar, and 7 is the final coating consisting of the benactyzine hydrochloride, the hydroxypropyl methyl cellulose-phthalate copolymer and the corn-starch.

EXAMPLE 3

Pop-rices obtained by a conventional exploding method under heat of moistened rice grains are coated with a 67% sugar syrup by means of a coating pan to produce a under sugar coating on the pop-rices each carrying about 2 mg of the sugar. The rice grains are further coated by spray-pan method with an acetone solution which has been prepared by dissolution of 2 parts of an acrylic acid-methacrylic acid copolymer in 98 parts of acetone, to produce an intermediate layer of coating layer weighing about 3 mg per rice grain of said acrylic and methacrylic acids copolymer.

The coated grains thus obtained are then treated with a liquid coating material consisting of 0.5 parts of benactyzine hydrochloride, 3.5 parts of a 67% sugar syrup, 6 parts of titanium oxide, 5 parts of ethyl cellulose and 85 parts of 1,1,1-trichloroethane to produce a final coating on the pop-rices, each of which carries about 2 mg of benactyzine hydrochloride.

The resulting coated grains are floatable in gastric juice for a long period of time while gradually releasing in the gastric juice the benactyzine hydrochloride dissolving out from the grains.

Figure 3:
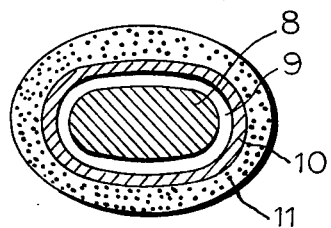

Accompanying FIG. 3 shows a sectional view of the coated product of this Example wherein 8 is the poprice grain, 9 is the under coating of sugar, 10 is the intermediate coating layer of the acrylic-methacrylic acids copolymer, and 11 is the final coating layer consisting of the benactyzine hydrochloride, sugar, titanium oxide and ethyl cellulose.

EXAMPLE 4

Pieces of concave shells of the same sizes each having the weight of 150 mg are formed by moulding under pressure with a powdery mixture consisting of 5 parts of propantheline bromide, 10 parts of finely pulverized refined sugar, 85 parts of pulverized ethyl cellulose and a minute quantity of magnesium stearate.

Each pair of the resulting shells are so arranged that the openings of the two pieces contact face-to-face, and the two pieces are then bonded in a solitary body with a bonding agent containing 10% ethyl cellulose dissolved in 1,1,1-trichloroethane to form the tablets having internal void. The individual inner voids of which being adjusted to take the space larger than ½ of the entire volume of the respective finished tablets.

The tablets thus obtained have the buoyancy floatable in gastric juice for a long period of time while gradually releasing in the gastric juice the propantheline bromide dissolving out from said finished tablets.

Figure 4:
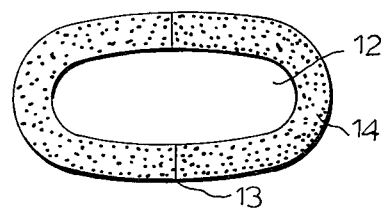

Accompanying FIG. 4 shows a sectional view of the resulting tablet according to this example, wherein 12 is the inner void, 13 is the joint of ethyl cellulose and 14 is the body of the tablet consisting of the propantheline bromide, the finely pulverized refined sugar, the finely pulverized ethyl cellulose and the magnesium stearate.

EXAMPLE 5

Tablets of flat disks each weighing approximate 30 mg are prepared by pressing in the moulds the powdery mixture together with a small amount of calcium stearate as additives, said powdery mixture in the sizes of 50–150 μ having been prepared by spray drying of a liquid mixture containing 18 parts of propantheline bromide, 2 parts of ethyl cellulose and 80 parts of 1,1,1-trichloroethane.

Separately, the external surfaces of the half-pieces of No. 4 hard capsules prescribed in Japanese Pharmacopoeia, the 8th edition, are coated spraying by a spray gun with a hydroxypropyl methyl cellulose-phthalate solution to produce the coated half pieces for the capsules each carrying 20 mg of the coating material.

Each of the openings of said coated half pieces are tamped with the aforementioned flat tablets and the gap between the contact area of the piece and the tamped tablet is sealed with a sealant of a 10% ethyl cellulose solution in 1,1,1-trichloroethane.

The resulting structural preparations possess buoyancy whereby the preparations are to be held in the gastric juice for a long period of time while the propantheline bromide as the active ingredient gradually releases therefrom into the gastric juice.

Figure 5:
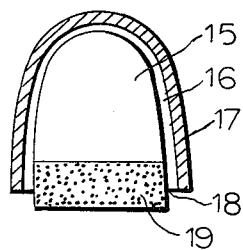

Accompanying FIG. 5 shows a sectional view of the resulting preparation in this Example, wherein 15 is the internal void, 16 is the half piece of No. 4 hard capsule, 17 is the crust of the hydroxypropyl methyl cellulose-phthalate coating, 18 is the bonded portion with the ethyl cellulose and 19 is the tablet in the form of disk consisting of a mixture of propantheline bromide, ethyl cellulose and calcium stearate.

EXAMPLE 6

External surfaces of No. 3 hard capsule prescribed in Japanese Pharmacopoeia, the 8th edition, are coated with a copolymer of acrylic and methacrylic acids to obtain under coating, each of said coatings weighing 10 mg.

The coated empty capsules as the nuclei are covered with films of gelatin using the plate process conventionally employed for the preparation of soft capsules, said films of gelatin having been obtained from an aqueous gelatin solution consisting of 35 parts of gelatin, 5 parts of glycerol, 2.5 parts of Food Yellow No. 4 (Tartrazine) under prescription by the Japanese Ministry of Hygiene and Health, which employed as a substitute of a pharmaceutically active ingredient, 7.5 parts of glucose and 50 parts of water to produce 150 mg of the coating of gelatin per capsule. The coated capsules are kept at 60°C. for 60 minutes for the aging of films.

The coated preparations thus obtained have the buoyancy whereby the preparations are to be held in gastric juice for a long period of time while the juice is gradually colored yellow due to successive releasing of the coloring material as the indicator in lieu of an active ingredient.

Figure 6:
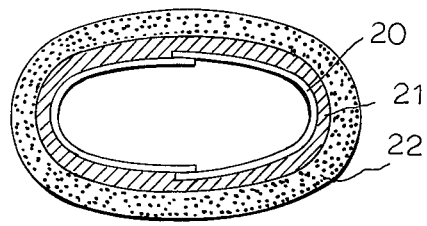

Accompanying FIG. 6 shows a sectional view of the product obtained in this Example wherein 20 is No. 3 hard capsule, 21 is the under coating of the acrylic and methacrylic acid copolymer, and 22 is the coating of gelatin, glycerol, Food Yellow No. 4 (Tartrazine) and glucose.

What is claimed is:

1. A solid therapeutic preparation adapted to be taken internally, which preparation is floatable in the gastric juices in the stomach and is characterized by remaining in the stomach for a long period of time while gradually releasing a therapeutically active ingredient contained therein into the gastric juices of the stomach, said preparation consisting essentially of a hollow pharmaceutically acceptable globular shell conventionally employed for internal therapeutic use containing coated on the external surface thereof an under-coating and a final coating, said under-coating being a layer of a cellulose acetate-phthalate copolymer and said final coating being a layer of ethyl-cellulose and hydroxylpropyl cellulose in combination with an effective amount of a pharmaceutically active ingredient selected from the group consisting of a gastric acid secretion inhibitor, a gastric acid neutralizer and an anti-pepsin inhibitor.

2. A solid therapeutic preparation as in claim 1 wherein the pharmaceutically active ingredient is selected from the group consisting of propantheline bromide and benactyzine hydrochloride.

3. A solid therapeutic preparation adapted to be taken internally, which preparation is floatable in the gastric juices in the stomach and is characterized by remaining in the stomach for a long period of time while gradually releasing a therapeutically active ingredient contained therein into the gastric juices of the stomach, said preparation consisting essentially of a small oval shaped nucleus of polystyrol foam of low apparent specific gravity externally coated with an under-coating and a final coating, said under-coating being a layer of sugar and said final coating being a layer of a hydroxypropyl methyl cellulose-phthalate copolymer in combination with corn-starch and an effective amount of a pharmaceutically active ingredient selected from the group consisting of a gastric acid secretion inhibitor, a gastric acid neutralizer and an anti-pepsin inhibitor.

4. A solid therapeutic preparation according to claim 3, wherein the active pharmaceutical ingredient is selected from the group consisting of propantheline bromide and benactyzine hydrochloride.

5. A solid therapeutic preparation adapted to be taken internally, which preparation is floatable in the gastric juices in the stomach and is characterized by remaining in the stomach for a long period of time while gradually releasing a therapeutically active ingredient contained therein into the gastric juices of the stomach, said preparation consisting essentially of a popped rice nucleus covered with an under-coating, an intermediate coating and a final coating, said under-coating being a layer of sugar, said intermediate coating being a layer of an acrylic and methacrylic acid copolymer, and said final coating being a layer of ethyl cellulose in combination with sugar, titanium oxide and an effective amount of a pharmaceutical agent selected from the group consisting of a gastric acid secretion inhibitor, a gastric acid neutralizer and an anti-pepsin inhibitor.

6. A solid therapeutic preparation according to claim 5 wherein the active pharmaceutical ingredient is selected from the group consisting of propantheline bromide and benactyzine hydrochloride.

7. A solid therapeutic globular tablet consisting essentially of two hollow cups joined together at the peripheries thereof by a bonding agent consisting essentially of ethyl cellulose, said hollow cups being composed of an effective amount of a therapeutically active ingredient selected from the group consisting of a gastric acid secretion inhibitor, a gastric acid neutralizer and an anti-pepsin inhibitor; pulverized sugar, pulverized ethyl cellulose and a minor amount of magnesium stearate.

8. A solid therapeutic preparation adapted to be taken internally, which preparation is floatable in the gastric juices in the stomach and is characterized by remaining in the stomach for a long period of time while gradually releasing a therapeutically active ingredient contained therein into the gastric juices of the stomach, said preparation consisting essentially of a flat disc shaped tablet bonded to the open ends of two half pieces of a cup shaped hard capsule so that the disc shaped tablet is encapsulated within the hard capsule in the center thereof, said disc shaped tablet consisting essentially of a therapeutically active ingredient consisting essentially of an effective amount of a gastric acid secretion inhibitor, a gastric acid neutralizer and an anti-pepsin inhibitor; pulverized ethyl cellulose and a minor amount of calcium stearate and wherein the external surface of the hard capsule is coated with a hydroxypropyl methyl cellulose phthalate.

9. A solid therapeutic preparation adapted to be taken internally, which preparation is floatable in the gastric juices in the stomach and is characterized by remaining in the stomach for a long period of time while gradually releasing a therapeutically active ingredient contained therein into the gastric juices of the stomach, which consists essentially of a hollow globular shell coated on the external surface thereof with an under-coating of an acrylic and methacrylic acid copolymer and a final coating consisting of gelatin, glycerol, glucose and an effective amount of a therapeutically active ingredient selected from the group consisting of a gastric acid secretion inhibitor, a gastric acid neutralizer and an anti-pepsin inhibitor, said hollow globular shell being a hard capsule conventionally employed for therapeutic internal use.

* * * * *